(12) United States Patent
Baranski

(10) Patent No.: US 7,342,126 B2
(45) Date of Patent: Mar. 11, 2008

(54) PROCESS FOR THE PREPARATION OF 4-OXO-4-((4-(PHENYLAMINO)PHENYL) AMINO)-2-BUTENOIC ACID

(75) Inventor: John R. Baranski, Southington, CT (US)

(73) Assignee: Crompton Corporation, Middlebury, CT (US)

( * ) Notice: Subject to any disclaimer, the term of this patent is extended or adjusted under 35 U.S.C. 154(b) by 369 days.

(21) Appl. No.: 10/977,618

(22) Filed: Oct. 27, 2004

(65) Prior Publication Data

US 2006/0089511 A1    Apr. 27, 2006

(51) Int. Cl.
    *C07C 229/00*    (2006.01)
(52) U.S. Cl. ...................................... 562/450
(58) Field of Classification Search .................. 562/450
    See application file for complete search history.

(56) References Cited

FOREIGN PATENT DOCUMENTS

GB           1307409            2/1973
WO       WO 03/099890 A2       12/2004

*Primary Examiner*—Taylor Victor Oh
(74) *Attorney, Agent, or Firm*—Jaimes Sher

(57) ABSTRACT

A process for the preparation of 4-oxo-4-((4-(phenylamino) phenyl)amino)-2-butenoic acid includes reacting p-aminodiphenyl amine and maleic anhydride in a reaction first mixture containing a volatile organic solvent under suitable reaction conditions to provide a second mixture containing 4-oxo-4-((4-(phenylamino)phenyl)amino)-2-butenoic acid product; subjecting the second mixture to vacuum distillation to remove the volatile organic solvent while simultaneously adding diluent oil to produce a dispersion of 4-oxo-4-((4-(phenylamino)phenyl)amino)-2-butenoic acid in the diluent oil.

13 Claims, 2 Drawing Sheets

PROCESS FOR THE PREPARATION OF 4-OXO-4-((4-(PHENYLAMINO)PHENYL) AMINO)-2-BUTENOIC ACID

BACKGROUND

1. Field of the Invention

The present invention relates to a method for making 4-oxo-4-((4-(phenylamino)phenyl)amino)-2-butenoic acid.

2. Background of the Art

4-Oxo-4-((4-(phenylamino)phenyl)amino)-2-butenoic acid is used in preparing high performance dispersants for lubricants. This material has very limited solubility in common organic solvents such as acetone, methylethyl ketone (MEK), methyl isobutyl ketone, ethyl acetate, butyl acetate, xylene, toluene, N-methylpyrrolidinone, and the like. The grafting process for preparing a lubricant dispersant from this compound does not lend itself well to processing volatile carrier solvents. At best, only about 30% to 40% by weight of butenoic acid can be loaded into the strongest solvents, and the use of volatile organic solvents also introduces hazards during the customers' use of the product.

What is needed is a process for making this compound that does not introduce volatile organic solvent in the final product.

SUMMARY

A process is provided herein for the preparation of 4-oxo-4-((4-(phenylamino)phenyl)amino)-2-butenoic acid. The process comprises reacting p-aminodiphenyl amine and maleic anhydride in a reaction first mixture containing a volatile organic solvent under suitable reaction conditions to provide a second mixture containing 4-oxo-4-((4-(phenylamino) phenyl)amino)-2-butenoic acid product; subjecting the second mixture to vacuum distillation to remove the volatile organic solvent while simultaneously adding diluent oil to produce a dispersion of 4-oxo-4-((4-(phenylamino) phenyl)amino)-2-butenoic acid in the diluent oil.

The process eliminates volatile solvent from the final product and also provides a stable dispersion for easy storage, transportation and handling of the compound.

BRIEF DESCRIPTION OF THE DRAWING(S)

Various embodiments are described below with reference to the drawings wherein.

DETAILED DESCRIPTION OF PREFERRED EMBODIMENT(S)

The preparation of 4-oxo-4-((4-(phenylamino)phenyl) amino)-2-butenoic acid [$C_6H_5NH-C_6H_4NH-C(O)-C=C-C(O)OH$] is prepared according to the following reaction scheme

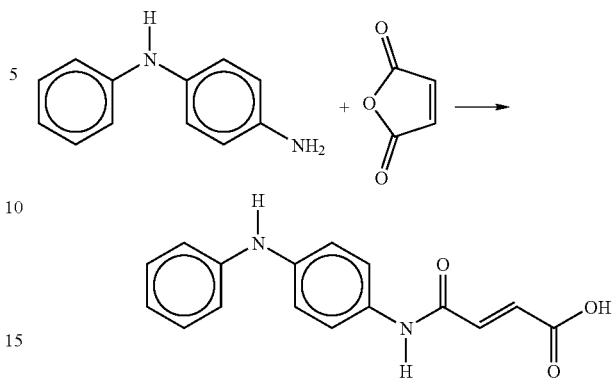

The reaction involves one equivalent of p-aminodiphenyl amine and one equivalent of maleic anhydride. The reaction is exothermic and conducted in a suitable solvent such as acetone, methylethyl ketone (MEK), methyl isobutyl ketone, ethyl acetate, methyl acetate, butyl acetate, xylene, toluene, N-methylpyrrolidinone, and the like. The product concentration in the reaction mass can range from about 10% to about 40% by weight depending on the chosen reaction solvent.

The reaction is typically conducted at a temperature of from about 50° C. to about 100° C., preferably from about 70° C. to about 80° C. A suitable reactor apparatus for conducting the reaction is illustrated in FIG. 1.

Figure 1:
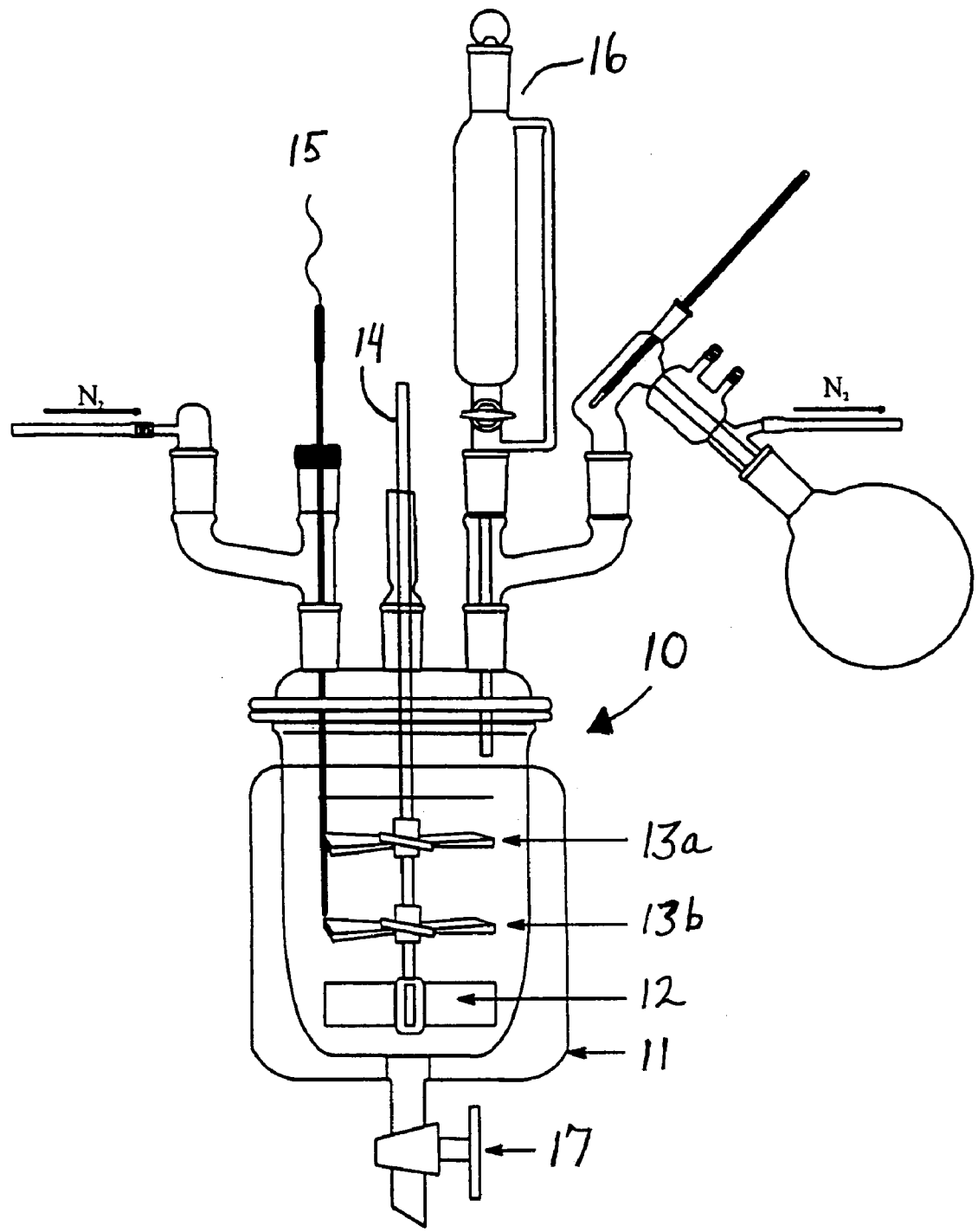
FIG. 1 is a diagrammatic illustration of a suitable reactor apparatus for performing the invention.
Figure 2:
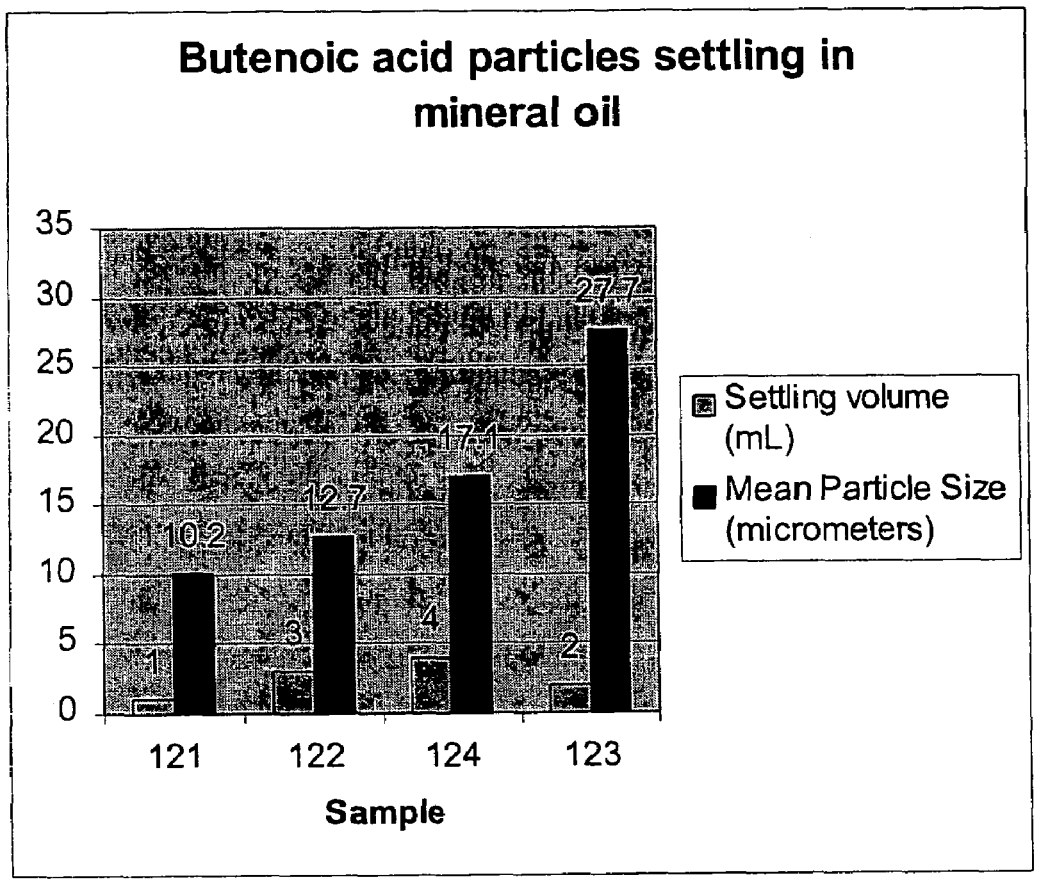
FIG. 2 is a graph illustrating the product settling in diluent oil for the examples presented below; and, FIG. 3 is a diagrammatic illustration of the apparatus utilized in the determination of particle settling tendencies.

Referring now to FIG. 1, a suitable apparatus includes a resin kettle reactor 10 having one or more turbines 13a and 13b and a paddle 12 mounted to a rotatable shaft 14 for agitation of the reactor con tents. The reactor is preferably provided with a heating/cooling jacket 11 for temperature control. Temperature is monitored with a thermocouple 15. Nitrogen is flashed through the system. The reactants are added by means of an addition funnel 16 and the product is withdrawn from the bottom of the reactor through bottom valve 17.

After the reaction is completed the contents of the reactor, which now contains 4-oxo-4-((4-(phenylamino)phenyl) amino)-2-butenoic acid and solvent, is subjected to vacuum distillation to remove the solvent. However, at the same time a diluent oil is introduced into the reactor to replace the solvent. The resulting product is a stable dispersion of 4-oxo-4-((4-(phenylamino)phenyl)amino)-2-butenoic acid in diluent oil.

As a less preferred alternative, the initial reaction contents can contain some diluent oil in addition to the reactants and organic solvent.

The diluent oil used in the synthesis process of the invention can be a natural oil, synthetic oil or mixture thereof. The natural oils that are useful include animal oils and vegetable oils (e.g., castor oil, lard oil) as well as mineral oils such as liquid petroleum oils and solvent treated or acid-treated mineral oils of the paraffinic, naphthenic or mixed paraffinic-naphthenic types. Oils derived from coal or shale are also useful. Synthetic oils include hydrocarbon oils such as polymerized and interpolymerized olefins (e.g., polybutylenes, polypropylenes, propylene isobutylene copolymers, etc.); poly(1-hexenes), poly-(1-octenes), poly (1-decenes), etc. and mixtures thereof; alkylbenzenes (e.g., dodecylbenzenes, tetradecylbenzenes, dinonylbenzenes, di-(2-ethylhexyl)benzenes, etc.); polyphenyls (e.g., biphenyls, terphenyls, alkylated polyphenyls, etc.); alkylated diphenyl ethers and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that can be used. These are exemplified by the oils prepared through polymerization of ethylene oxide or propylene oxide, the alkyl and aryl ethers of these polyoxyalkylene polymers or mono- and polycarboxylic esters thereof, for example, the acetic acid esters, mixed $C_{3-8}$ fatty acid esters, or the $C_{13}$ Oxo acid diester of tetraethylene glycol.

Another suitable class of synthetic oils that can be used comprises the esters of dicarboxylic acids (e.g., phthalic acid, succinic acid, alkyl succinic acids, alkenyl, succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

The oil can be a polyalphaolefin (PAO). Typically, the PAOs are derived from monomers having from about 4 to about 30, or from about 4 to about 20, or from about 6 to about 16 carbon atoms. Examples of useful PAOs include those derived from octene, decene, mixtures thereof, and the like. Mixtures of mineral oil with one or more of the foregoing PAOs may be used.

The following examples illustrate the invention.

EXAMPLES

The maleic anhydride (2.24 mol) and ethyl acetate (1200 grams) were charged to a 1-liter bottom-out resin kettle reactor equipped with an overhead stirrer, thermocouple, and a short-path distillation condenser. The reactor contents were heated to 50-55° C. The molten (75-80° C.) p-aminodiphenyl amine (2.24 mol) was slowly added to the reactor from a pressure-equalizing addition funnel over a 30-minute period. The exotherm brought the reaction temperature to 75° C. After all the amine was added, the system was post-reacted at 75° C. for 4-hours. The ethyl acetate was removed by vacuum distillation. As the ethyl acetate was removed, 1675 grams of Prorex 100 mineral oil was slowly added as a replacement. The final product, a creamy, orange dispersion, was drained from the reactor.

Four batches of butenoic acid were prepared under varied reaction conditions. Three of the batches utilized low levels of mineral oil during the reaction. The oil level in the reactor was varied to determine if it were possible to reduce the level of solvent used during the reaction and also to determine the effect on particle size. The ratio of ethyl acetate (grams) to mineral oil (grams) present during the reaction was varied from 1:0 to 1.62:1 (see Table 1). These varied conditions produced a product with varied particle sizes (see Table 2). Solids from each batch were isolated by vacuum filtration of 100-gram samples, washed several times with heptanes, and vacuum dried. The product concentration of each batch was calculated and the solids were analyzed by HPLC and for particle size.

TABLE 1

(Reactor loadings and percent solids data.)

| Sample | Ethyl acetate grams in reaction | Mineral oil grams in reaction | Mineral oil grams added at end of RXN | Total mineral oil grams added | Actual percent solids of batch |
|---|---|---|---|---|---|
| 121 | 525 | 0 | 869 | 869 | 27.8 |
| 122 | 525 | 50 | 819 | 869 | 26.2 |
| 123 | 425 | 100 | 769 | 869 | 24.7 |
| 124 | 324 | 200 | 669 | 869 | 27.1 |

TABLE 2

(Settling and particle size data.)

| Sample | Settling volume (mL) | Mean Particle Size (micrometers) |
|---|---|---|
| 121 | 1 | 10.2 |
| 122 | 3 | 12.7 |
| 124 | 4 | 17.1 |
| 123 | 2 | 27.7 |

Particle size was determined using a Horiba LA-910 laser scattering particle distribution analyzer. Laser light irradiating the particles is scattered at various angles. If the particles are large, the scattering is concentrated in the forward direction; conversely, if the particles are small, the scattering is in all directions. Therefore, to measure larger particles, data on the scattered light intensity of a small angle is needed; to measure smaller particles, data on the intensity of a large angle is needed. To measure the distribution of small-angle scattered light intensity from the sample particles, the LA-910 uses a condenser lens to condense the light on a ring-type detector. For larger-angle scattered light intensity, detectors are located at the side and rear.

From the angular distribution of the scattered light intensity, the Mie scattering theory is used to calculate the particle-size distribution.

Figure 3:
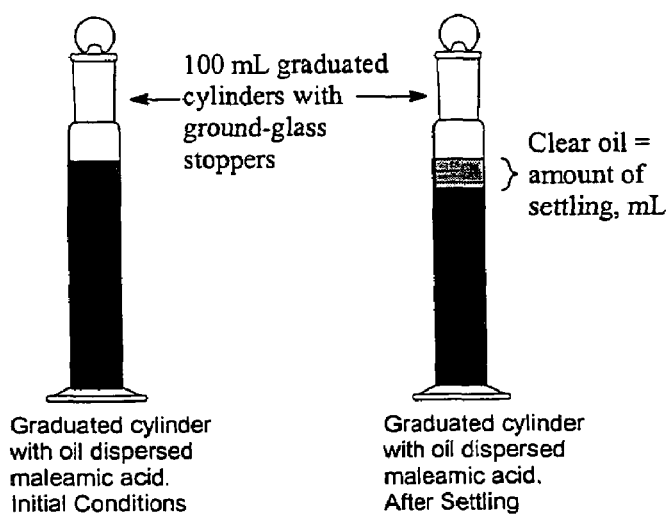

Referring now to FIG. 3, the settling tendency of each batch was determined by the following procedure: 100 mL of each well-mixed batch was placed in a 100 mL graduated cylinder equipped with a ground glass stopper as shown in FIG. 3. The amount of oil visible at the top of each sample (i.e., the settling volume in mL) was observed and recorded over a 4 month period. The final settling volume was then graphed versus particle size.

The amount of observed settling increased with particle size until the particles were about 17 micrometers. A decrease in settling volume was then observed. The large particles in sample 123 tended to agglomerate together in the reactor and in the solution. This agglomerization probably helped retard settling. However, these agglomerizations were often manifested as chunks. A dispersion containing particles with these characteristics would be difficult to pump and the long-term stability of the dispersion would be suspect.

The sample containing the smallest particle size (121) exhibited the best physical characteristics, i.e. smooth consistency, moderate viscosity, no agglomerations and low settling tendencies.

While the above description contains many specifics, these specifics should not be construed as limitations of the invention, but merely as exemplifications of preferred embodiments thereof. Those skilled in the art will envision many other possibilities within the scope and spirit of the invention as defined by the claims appended hereto.

What is claimed is:

1. A process for the preparation of 4-oxo-4-((4-(phenylamino)phenyl)amino)-2-butenoic acid which comprises: reacting p-aminodiphenyl amine and maleic anhydride in a reaction first mixture containing a volatile organic solvent under suitable reaction conditions to provide a second mixture containing 4-oxo-4-((4-(phenylamino)phenyl)amino)-2-butenoic acid product; subjecting the second mixture to vacuum distillation to remove the volatile organic solvent while simultaneously adding diluent oil to produce a dispersion of 4-oxo-4-((4-(phenylamino)phenyl)amino)-2-butenoic acid in the diluent oil.

2. The process of claim 1 wherein reaction conditions include a temperature of from about 50° C. to about 100° C.

3. The process of claim 1 wherein the reaction conditions include a temperature of from about 70° C. to about 80° C.

4. The process of claim 1 wherein the volatile organic solvent is acetone, methylethyl ketone, methyl isobutyl ketone, ethyl acetate, methyl acetate, butyl acetate, xylene, toluene, or N-methylpyrrolidinone.

5. The process of claim 1 wherein the diluent oil is a natural oil selected from the group consisting of animal, vegetable and mineral oils.

6. The process of claim 5 wherein the natural oil is a vegetable oil.

7. The process of claim 5 wherein the mineral oil is selected from the group consisting of paraffinic, naphthenic and mixed paraffinic-naphthenic oils.

8. The process of claim 1 wherein the diluent oil is a synthetic oil.

9. The process of claim 8 wherein the synthetic oil is a polyalphaolefin oil.

10. The process of claim 8 wherein the polyalphaolefin is derived from monomers having from about 4 to about 30 carbon atoms.

11. The process of claim 8 wherein the synthetic oil is an ester oil.

12. The process of claim 11 wherein the ester oil is derived from (i) an acid selected from the group consisting of phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acid, and alkenyl malonic acid, and (ii) an alcohol selected from the group consisting of butyl alcohol, hexyl alcohol, dodecyl alcohol, 2-ethylhexyl alcohol, ethylene glycol, diethylene glycol monoether and propylene glycol.

13. The process of claim 8 wherein the synthetic oil is selected from the group consisting of alkylaromatic compounds, polyphenyls and alkylated diphenyl ethers.

* * * * *